(12) United States Patent
Capek et al.

(10) Patent No.: US 10,052,145 B2
(45) Date of Patent: Aug. 21, 2018

(54) ENGAGEABLE SLAPHAMMER TOOL AND INSTRUMENTATION

(71) Applicant: Zimmer, Inc., Warsaw, IN (US)

(72) Inventors: Joseph C. Capek, Granger, IN (US); Peter Darrigan, Fort Wayne, IN (US); Justin J. May, Leesburg, IN (US)

(73) Assignee: Zimmer, Inc., Warsaw, IN (US)

( * ) Notice: Subject to any disclaimer, the term of this patent is extended or adjusted under 35 U.S.C. 154(b) by 29 days.

(21) Appl. No.: 13/758,605

(22) Filed: Feb. 4, 2013

(65) Prior Publication Data

US 2013/0204265 A1 Aug. 8, 2013

Related U.S. Application Data

(60) Provisional application No. 61/595,274, filed on Feb. 6, 2012.

(51) Int. Cl.
| | |
|---|---|
| *A61B 17/92* | (2006.01) |
| *A61F 2/46* | (2006.01) |
| *A61B 17/00* | (2006.01) |
| *A61F 2/30* | (2006.01) |

(52) U.S. Cl.
CPC .............. *A61B 17/92* (2013.01); *A61F 2/461* (2013.01); *A61B 2017/00469* (2013.01); *A61B 2017/00473* (2013.01); *A61B 2017/00477* (2013.01); *A61F 2/4684* (2013.01); *A61F 2002/30426* (2013.01); *A61F 2002/4619* (2013.01); *A61F 2002/4681* (2013.01)

(58) Field of Classification Search
CPC ............. A61F 2002/4681; A61B 17/92; A61B 2017/922

USPC .......... 606/99, 100, 914–946; 81/27; 173/91
See application file for complete search history.

(56) References Cited

U.S. PATENT DOCUMENTS

| | | | |
|---|---|---|---|
| 4,222,382 A | 9/1980 | Antonsson et al. | |
| 4,399,813 A | 8/1983 | Barber | |
| 4,483,058 A * | 11/1984 | Clutter | B25B 27/02 29/254 |
| 4,703,549 A * | 11/1987 | Grandt | 29/426.5 |
| 4,993,410 A | 2/1991 | Kimsey | |

(Continued)

OTHER PUBLICATIONS

"Smith & Nephew Renovation Implant Removal System—Surgical Technique", Product Brochure, (2009), 20 pgs.

(Continued)

*Primary Examiner* — Olivia C Chang
(74) *Attorney, Agent, or Firm* — Schwegman Lundberg & Woessner, P.A.

(57) ABSTRACT

A slap hammer tool and associated instrumentation to engage with the slap hammer tool are disclosed herein. In some examples, a slap hammer tool including an end adapted for engagement with a quick release connector of an instrument is provided. The instrument can be adapted to receive the distal end of the slap hammer for engagement, the engagement being provided through rotation of the slap hammer relative to the instrument. Once the slap hammer and instrument are engageably coupled, the slap hammer can be used to provide force and accompanying motion away from the instrument in the direction of the slap hammer instrument. Force can be provided by the slap hammer tool to a coupled instrument, for example, to move or extract the coupled instrument from placement on a surgical area.

15 Claims, 6 Drawing Sheets

(56) References Cited

U.S. PATENT DOCUMENTS

| | | | |
|---|---|---|---|
| 5,290,291 A | 3/1994 | Linden | |
| 6,226,948 B1* | 5/2001 | Trout | 52/514.5 |
| 6,709,439 B2 | 3/2004 | Rogers et al. | |
| 2004/0193176 A1 | 9/2004 | Gerngross et al. | |
| 2008/0257113 A1* | 10/2008 | Neumarkel | 81/27 |
| 2010/0331851 A1 | 12/2010 | Huene | |

OTHER PUBLICATIONS

"Zimmer Trabecular Metal Reverse Shoulder System—Surgical Technique", Product Brochure 97/4309-103-00 Rev. 1 1009-E09 5ML, (2010), 36 pgs.

"Gorski Hip Cup Extraction Hook", Designed by Jerrold Gorski, MD; Innomed, (2012), 1 pg.

"Universal Modular Femoral Hip Component Extractors", Innomed, (2012), 1 pg.

"Zimmer Gender Solutions Natural-Knee Flex System Surgical Technique for Fixed and Rotating Platform", Zimmer, (Sep. 2009), 36 pgs.

"Zimmer M/L Taper Hip Prosthesis with Kinectiv Technology Surgical Technique", Zimmer, (Jul. 13, 2007), 22 pgs.

\* cited by examiner

ND INSTRUMENTATION

CLAIM OF PRIORITY

This application claims the benefit of priority under 35 U.S.C. § 119(e) of Capek et al., U.S. Provisional Patent Application Ser. No. 61/595,274, entitled "ENGAGEABLE SLAPHAMMER TOOL AND INSTRUMENTATION", filed on Feb. 6, 2012, which is incorporated by reference herein in its entirety.

BACKGROUND

During orthopedic procedures such as hip replacement or knee replacement surgeries, various tools and instruments are used to assist with the various procedures that shape the bone and establish an area for the insertion of a joint replacement implant. Some of the tools used during these procedures are designed to provide force in connection with one or more instruments, and to generally modify and verify the surgical area to accept the implant apparatus, for example with use of cutting guides, provisional fittings, pins, and other instruments. Force may be required to be applied towards, or away from, the surgical area in order to shape the surgical area, or to insert or extract various instruments and components involved in the surgical procedure.

For example, one tool used to apply force towards or away from a surgical area in a joint replacement procedure is known as a "slaphammer" or "slap hammer". Slap hammers, also known by the alternate name of a "slide hammer", provide a weight capable of sliding about a guide rod. The sliding weight can be used to generate a force when the sliding weight reaches and strikes a stop provided on the guide rod. For example, a slap hammer tool can be used to provide force downward towards an object, to provide precision force (e.g., impact) towards a point of interest at an end of the slap hammer. Likewise, a slap hammer tool can be used to provide force away from an object, such as to extract an object coupled to an end of the slap hammer tool.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Configurations and methods of use for a slap hammer tool and associated instruments configured to couple with the slap hammer tool are generally disclosed herein. In one example, a slap hammer is configured for engagement and disengagement with an instrument or other object used in connection with a surgical procedure. For example, an engagement of the slap hammer with a surgical object can be used to extract, reposition, place, or otherwise modify a location of the surgical object.

The engagement and disengagement mechanism within the instrument can be provided by use of a releasable coupling, allowing a connection to be established with a slap hammer tool that is easily, quickly, and reliably attachable to and removable from the instrument. A releasable coupling can be provided at one or more locations on the instrument, allowing the slap hammer tool to provide force at a specific location of the instrument.

In some examples, the releasable coupling can be provided by one or more quick-connect receptacles of an instrument that can be brought into coupling engagement or disengagement via insertion and rotational movement of the slap hammer tool. Upon establishment of the releasable coupling, the slap hammer tool can be operated to provide force with the instrument in a desired direction. Upon completion, the slap hammer tool can be operated to disestablish the releasable coupling and detach from the instrument.

Figure 1:
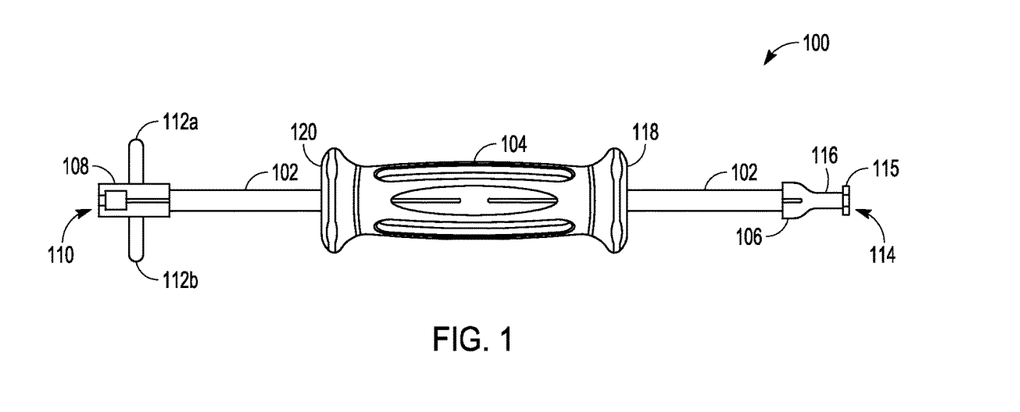
FIG. 1 illustrates a slap hammer tool configured for engageable mating with an instrument according to an example.

FIG. 1 depicts a representation of a slap hammer tool 100 configured for engageable mating with an instrument according to some examples. Specifically, as further described herein, the slap hammer tool 100 can include an engagement member 114 located at a first connectable end of the slap hammer tool 100. The engagement member 114 can be configured for coupling or attaching to an instrument, thereby allowing the slap hammer tool 100 to apply force to the instrument in connection once engageably coupled thereto.

As illustrated, the slap hammer tool 100 can include a rod or shaft 102 extending between stops 106, 108 located at a first end and a second end, respectively, of the shaft 102. The slap hammer tool 100 can also include a slideable member in the form of a handle 104 that can be configured for sliding along the shaft 102 between the stops 106, 108. In an example, the handle 104 can include a first handle end 118 and a second handle end 120. The handle 104 can further include a series of weights within the handle 104 that surround the shaft 102. Therefore, as the handle 104 is slid by an operator from a first end of the shaft 102 at or near the stop 106 to a second end of the shaft 102 at or near the stop 108, the second handle end 120 can make contact with the stop 108. With this contact, a force in the direction of the handle motion can be applied to the stop 108, the force continuing towards a second connectable end 110 of the slap hammer tool 100.

The slap hammer tool 100 can also be configured to provide force in the opposite direction. For example, if the handle 104 is slid by an operator from a second end of the shaft 102 at or near the stop 108 to a first end of the shaft 102 at or near the stop 106, the first handle end 118 can make contact with the stop 106. With this contact, a force in the direction of the handle motion can be applied to the stop 106, the force continuing towards the first connectable end (the engagement member 114) of the slap hammer tool 100 to cause impact on the coupled object.

Alternatively or in addition to the previously described illustration, the slap hammer tool 100 can provide a fixed striking or stopping member located along the shaft 102 within an interior space of the handle 104. This configuration, shown in more detail in cut-away illustrations in FIGS. 6A and 6B, can allow additional force or exclusive force to be provided on the striking or stopping member located within the middle of the shaft 102. Thus, the striking or stopping member can be located at a position between the first end and the second end of the shaft 102.

Figure 3A:
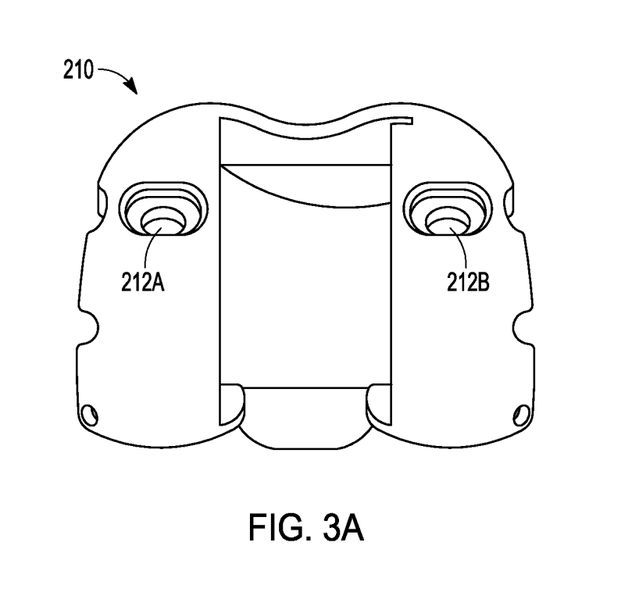
FIGS. 3A and 3B illustrate a femoral provisional instrument and femoral cut guide instrument respectively, each configured for mating with a connectable end of a slap hammer tool according to an example.
Figure 3B:
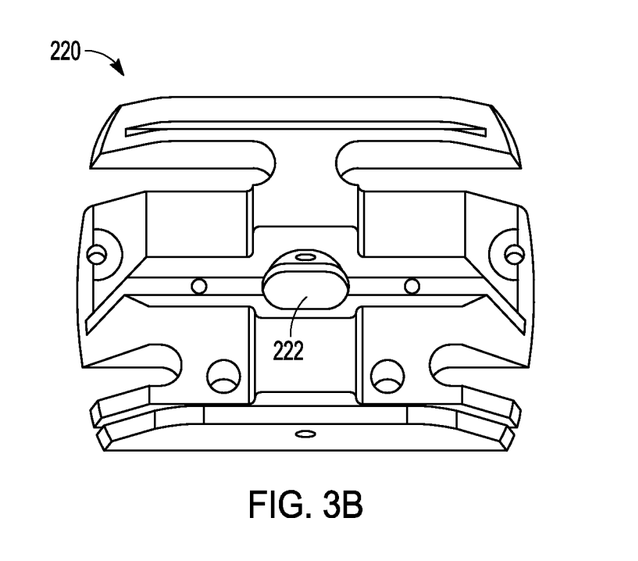
Figure 4:
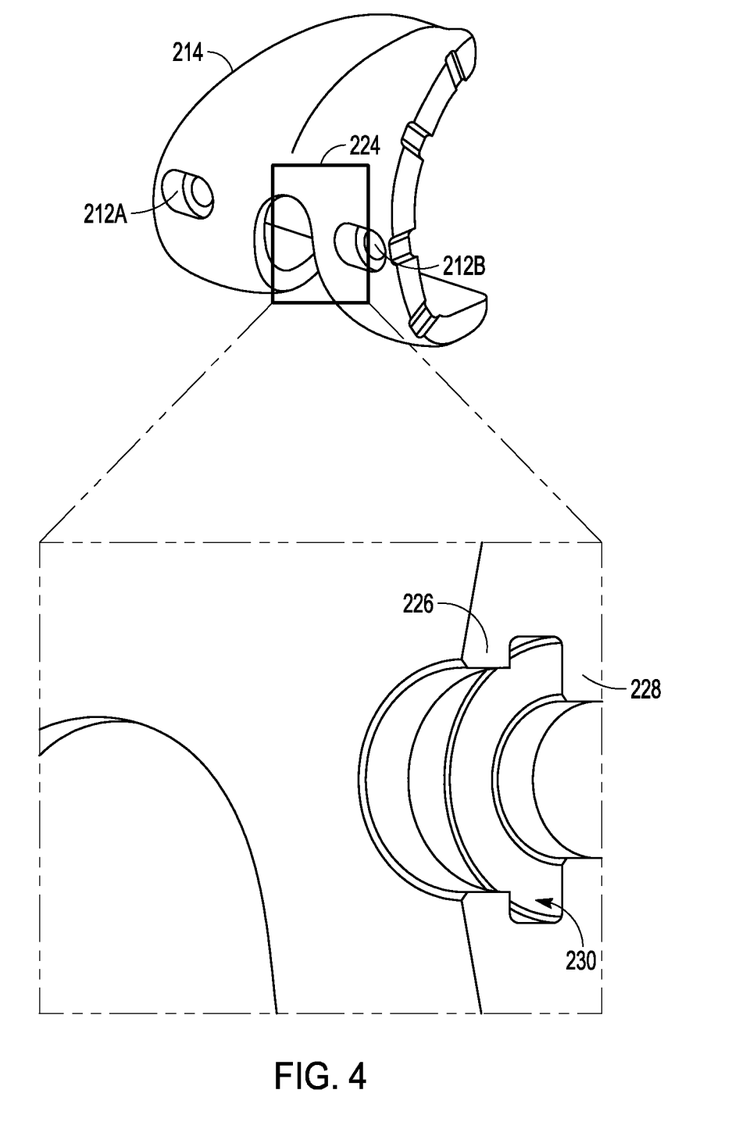
FIG. 4 illustrates a close-up view of a quick-connect receptacle in a femoral provisional instrument configured to receive a connectable end of a slap hammer tool according to an example.

As illustrated, in an example the engagement member 114 located at the end of the slap hammer tool 100 and coupled to the stop 106 can include a shaft 116 and an elongated connector 115 configured for coupling with a quick-connect mechanism. The elongated connector 115 can be specifically configured for insertion and rotation within a quick-connect mechanism to establish a coupling of an object with the slap hammer tool 100. FIGS. 3A, 3B, and 4 provide a more detailed illustration of an example quick-connect mechanism. FIG. 6B provides a further illustration of a location of the shaft 116 and the elongated connector 115 when coupled to a quick-connect mechanism.

Figure 2:
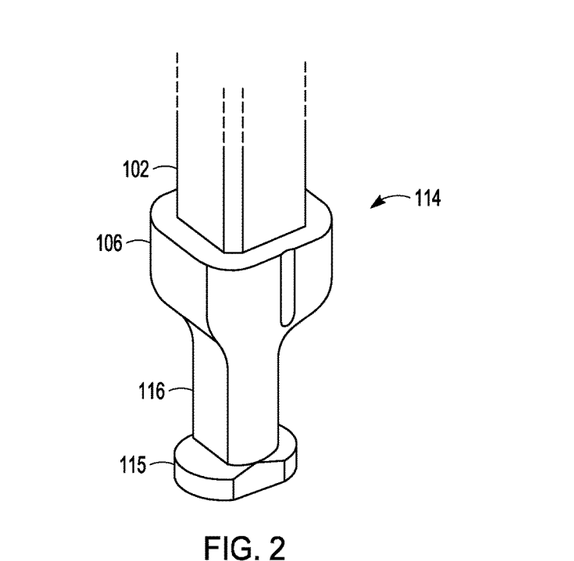
FIG. 2 illustrates a close-up view of a connectable end of a slap hammer tool configured for engageable mating with an instrument according to an example.

FIG. 2 illustrates a close-up view of the engagement member 114 of the slap hammer tool 100, which can be configured for engageable mating with a receiving instrument, such as an instrument providing a quick-connect mechanism. In an example, the engagement member 114 can be coupled to the stop 106, which in turn can be coupled to the shaft 102. As shown, the engagement member 114 can be provided with a suitable exterior shape that allows for insertion, rotation, and connection within a coupling mechanism. FIG. 2 illustrates the engagement member 114 having a shaft 116 extending beyond the stop 106, with attachment to an elongated connector 115. FIG. 2 also illustrates the shape of the elongated connector 115 being configured for insertion, rotation, and connection within a channel of a quick-connect receptacle or other coupling mechanism.

In some examples, the removability and attachment of the engagement member 114 from or to another object, respectively, can be provided by one or more quick-connect mechanisms in the object, such as ¼-, ½-, or ¾-turn fasteners, cam fasteners, sliding fasteners, or push-button fasteners configured to receive the engagement member 114 of the slap hammer tool 100. In some examples, simple rotational activating movement of the engagement member 114 can allow engagement and coupling to the object, when inserted into and operated with the one or more quick-connect receptacles of the object. Likewise, through the opposing rotational activating movement of the one or more quick-connect mechanisms, such as by counter-rotation of the slap hammer tool 100, the slap hammer tool 100 can be disengaged from the instrument.

FIGS. 3A and 3B illustrate a femoral provisional implant 210 and a femoral cut guide 220 respectively, each configured for coupling with an engagement feature at a connectable end of a slap hammer tool according to an example. For example, the femoral provisional implant 210 or the femoral cut guide 220 can be releasably coupled to the slap hammer instrument via one or more quick-connect mechanisms embodied within the provisional components, as further described herein. Although provisional components are depicted, those skilled in the art would recognize that this system can be adapted for use with non-provisional components, such as reusable implants and instruments.

Specifically, as illustrated in FIG. 3A, the femoral provisional implant 210 can be provided for use in an orthopedic procedure to replicate the characteristics of a corresponding non-provisional femoral prosthesis for implant (not shown). During the orthopedic procedure, the femoral provisional implant 210 can be placed on the surgical area, for example, to test out the size and fit for the prosthesis. Once the fitting and other uses of the femoral provisional implant 210 are complete, the femoral provisional implant 210 can be removed from the surgical area.

In some examples, removal of the femoral provisional instrument 210 can be facilitated through connection of a slap hammer tool to one or more quick-connect receptacles. For example, FIG. 3A depicts two receptacles 212A, 212B each configured to receive an engagement feature of a slap hammer tool, for example the slap hammer tool 100 depicted in FIG. 1. Specifically, the receptacles 212A, 212B can each provide a quick-connect mechanism for receipt of the engagement member 114 of the slap hammer tool 100.

In an example, the quick-connect connectors can be a rotatable fastener such as ¼-, ½-, or ¾-turn fasteners configured to receive a engagement feature of a slap hammer tool and facilitate movement with the turn of the slap hammer tool. Other quick-release connectors which can be provided for engageable coupling include cam fasteners, sliding fasteners, push-button fasteners or the like.

The connector receptacles 212A, 212B can be configured (e.g., include internal threads, channels, or mechanisms) to engage the engagement feature of the slap hammer tool when the slap hammer tool or a connector rotatable by the slap hammer tool is rotated in a first engaging direction (e.g., a clockwise direction). In a similar manner, the connector receptacles 212A, 212B can be configured to disengage the engagement feature of the slap hammer tool when the slap hammer tool a connector rotatable by the slap hammer tool is rotated in a second disengaging direction (e.g., a counter-clockwise direction).

FIG. 3B depicts one receptacle 222 in the femoral cut guide 220 configured to receive an engagement feature of a slap hammer tool according to some examples. As illustrated, the one receptacle 222 provides an elongated opening to receive the engagement feature of the slap hammer tool at a particular orientation. Once the engagement feature of the slap hammer tool is inserted into the elongated opening of the receptacle 222, the slap hammer tool can be provided at another orientation to engage a connection mechanism within the receptacle 222. For example, once inserted into the elongated opening, a quarter-turn rotation of the slap hammer tool can be sufficient to engage the connection mechanism and couple the femoral cut guide 220 to the slap hammer tool.

FIG. 4 illustrates a close-up view 224 of a quick-connect receptacle 212B in a cruciate-retaining femoral provisional implant 214 configured to receive a connector located at connectable end of a slap hammer tool according to some examples. As shown, the quick-connect receptacle 212B can include an opening 226 configured to receive insertion of the connectable end of the slap hammer tool at a first orientation. The connectable end of the slap hammer tool can be inserted into the opening 226 and extended into the quick-connect receptacle 212B until reaching a stop provided by a stop 228. Although the stop provided by stop 228 is depicted as providing a small circular opening, in some examples, no opening may be provided.

Between the opening defined by opening 226 and the stop defined by stop 228, a channel 230 can be established. Specifically, the channel 230 can be configured at an opposite orientation as the opening provided by opening 226. This opposite orientation in the channel 230 can enable the slap hammer tool 100 to be rotated from a first orientation into a second orientation. For example, a slap hammer tool inserted into the quick-connect receptacle 212B to couple the connectable member within the channel 230, can be rotated from a first orientation to a second orientation. This rotation can then move the connectable member within the channel 230 to a portion where the connectable member will be surrounded by stops provided by the opening 226 and stop 228, thereby providing a coupling between the connectable member of the slap hammer tool and the instrument.

It will be understood that variations to the presently described quick-connect receptacle and slap hammer tool connectable end can be provided to support other mechanisms and connection types. For example, a cam-type fastener can be provided within a channel of a quick-connect receptacle to rotate into disengaging and engaging positions. Other types of rotatable connection mechanisms allowing engagement and disengagement can likewise be seated within a channel of a quick-connect receptacle.

FIGS. 5A, 5B, 5C, and 5D illustrate a sequence of operations to connect a slap hammer tool 100 with another instrument, specifically a cruciate-retaining femoral provisional implant 214. As illustrated, the engagement member 114 of the slap hammer tool 100 can be aligned with, inserted into, and rotated while in a quick-connect receptacle 212B of the femoral provisional implant 214, resulting in a coupling that enables extraction of the femoral provisional implant with force applied from the slap hammer tool 100.

Figure 5A:
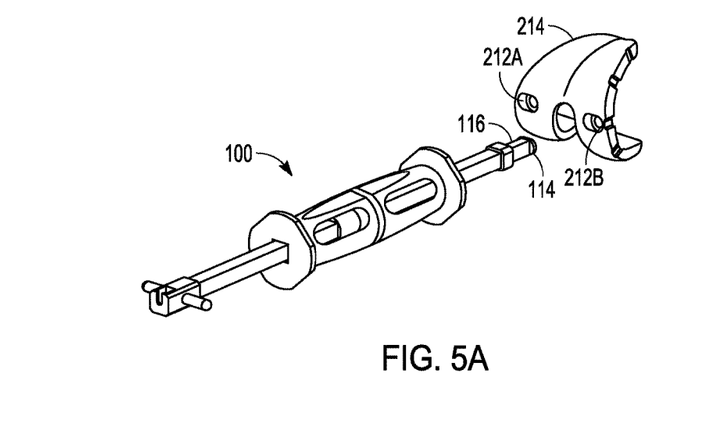
FIGS. 5A, 5B, 5C, and 5D illustrate alignment, insertion, rotation, and extraction motion of a slap hammer tool configured for engageable mating with a femoral provisional instrument according to an example.

FIG. 5A first illustrates the alignment of the slap hammer tool 100 for coupling with the femoral provisional implant 214. Specifically, the engagement member 114, located at the distal end of the slap hammer tool 100, can initially be oriented for placement (e.g., insertion) into the quick-connect receptacle 212B.

Figure 5B:
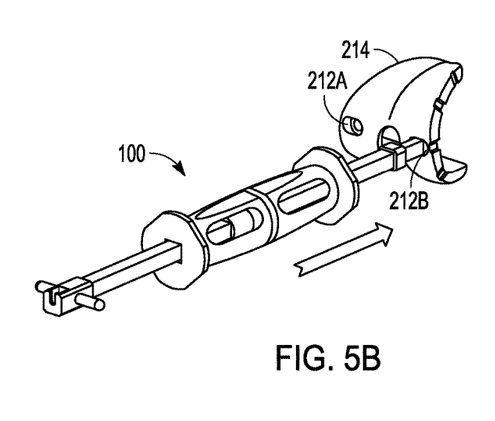

FIG. 5B illustrates the insertion of the engagement member 114 located at the distal end of the slap hammer tool 100 into the quick-connect receptacle 212B. The slap hammer tool 100 can be inserted until reaching an end stop of the quick-connect receptacle 212B. As shown, the shaft 116 extending from the end of the engagement member 114 may not be fully inserted into the quick-connect receptacle 212B of the femoral provisional implant 214. In alternate examples, the quick-connect receptacle 212B can receive an entirety of the shaft 116, thereby accepting most or all of the engageable end of the slap hammer tool 100.

Figure 5C:
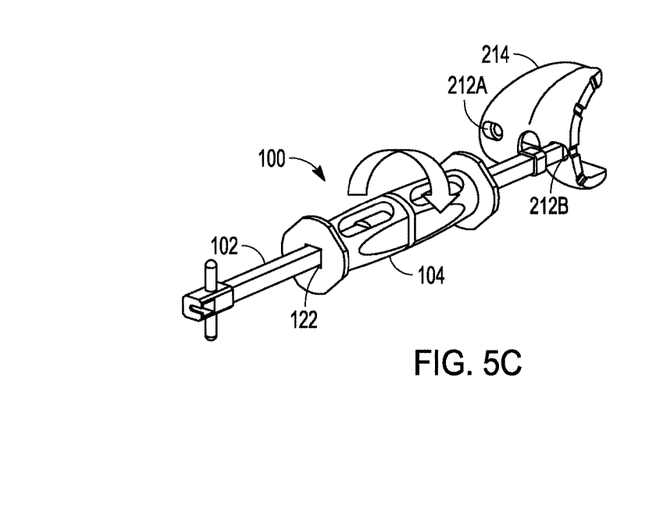

FIG. 5C illustrates the result of rotation of the slap hammer tool 100 relative to the femoral provisional implant 214, after the slap hammer tool 100 has been inserted into the quick-connect receptacle 212B. For example, a comparison of FIG. 5B with FIG. 5C will indicate a rotation of the slap hammer tool 100 occurring in a clockwise direction in the amount of a quarter turn. Although the rotation is illustrated as being performed in a clockwise direction, the quick-connect receptacle 212B can also be configured to allow rotation in a counter-clockwise direction. Likewise, although the rotation is illustrated as being performed only in a quarter-turn rotation, the amount of rotation can be dependent on the type or configuration of the mechanism within the quick-connect receptacle 212A, 212B. For example, the quick-connect receptacle connector may require a ½, ¾, or other fractional turn.

In an example, the handle 104 provided within the slap hammer tool 100 can be configured to slide about the shaft 102, while still enabling rotation of the entire tool. This can be facilitated, for example, by a defined shape (e.g., keyed shape) of the shaft 102 and handle 104 which allows rotation of both components. For example, as shown in FIG. 5C, the corresponding square shape of the shaft 102 and the shaft opening 122 in the handle 104, enables the square-shaped shaft 102 to extend through the handle 104. Therefore, the rotation of the handle 104 engages the shaft 102 to rotate the entire slap hammer tool 100 in a desired direction.

Figure 5D:
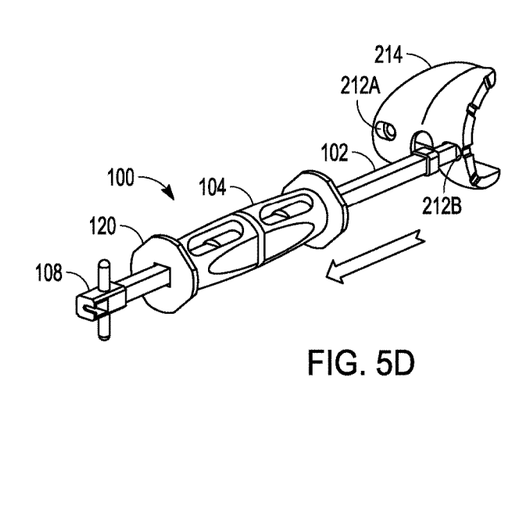

FIG. 5D illustrates a use of the slap hammer tool 100 to extract the femoral provisional implant 214 from placement on a surgical location, once the slap hammer tool 100 is engageably coupled to the femoral provisional implant 214. Specifically, FIG. 5D shows use of the slap hammer tool 100 by providing a force in a direction away from the femoral provisional implant 214 to extract or otherwise pull the femoral provisional implant 214 in the direction of motion. As shown, the second handle end 120 can be configured to strike or otherwise make contact with the stop 108 at the opposite end of the coupling to the femoral provisional implant 214. This action can result in a force on the slap hammer tool 100, and thus the coupled femoral provisional implant 214, in a direction distal of the coupled area of the femoral provisional implant 214.

The slap hammer force action therefore enables extraction or like movement of the femoral provisional implant 214 from the surgical area or other area of interest that it is located at or mounted to. Further, the engageable coupling between the slap hammer tool 100 and the femoral provisional implant 214 can be maintained once the femoral provisional implant 214 is moved. For example, the femoral provisional implant 214 can remain coupled to the slap hammer tool 100 and will not fall or immediately disengage from the slap hammer tool 100 once the femoral provisional implant 214 is extracted from the surgical area. To remove the femoral provisional implant 214, a counter rotation to the rotation depicted in FIG. 5C can be used to release the quick-coupling mechanism.

Figure 6A:
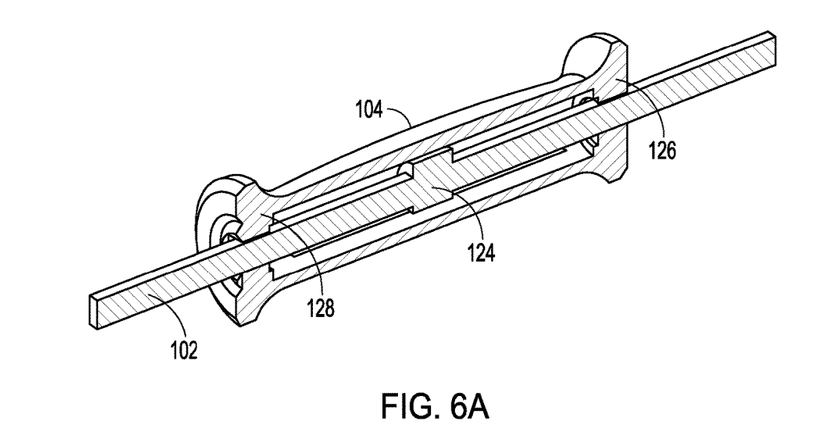
FIG. 6A illustrates a cut-away view of a slap hammer tool providing a striking member relative to a sliding member according to an example.
Figure 6B:
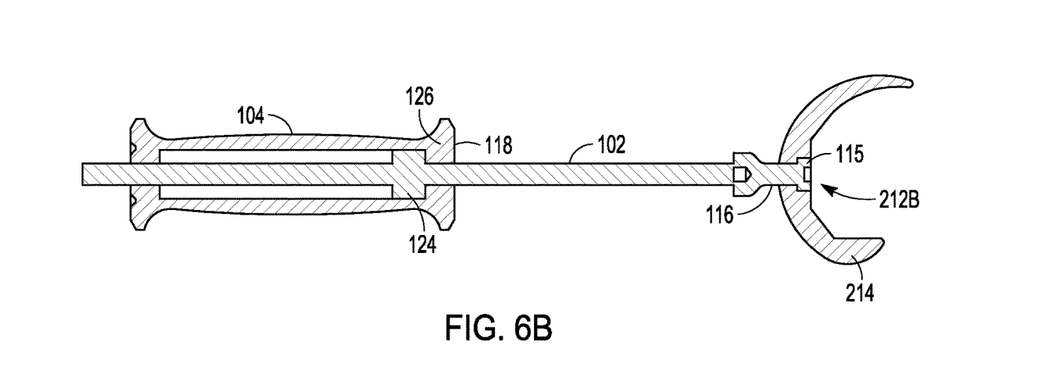
FIG. 6B illustrates a cut-away view of a slap hammer tool engageably coupled to a femoral provisional instrument and providing contact between the striking member and sliding member according to an example.

FIG. 6A illustrates a cross-section view of a slap hammer tool providing a striking member 124 relative to a set of sliding members 126, 128 according to an example, and further to the previous descriptions. Thus, the striking member 124 which receives the force of the slap hammer tool can be located along the shaft 102 within an interior cavity of the handle 104.

FIG. 6B illustrates a cross-section view of a slap hammer tool engageably coupled to a femoral provisional implant 214 and providing contact between the striking member 124 and the sliding member (handle 104) according to an example. This cross-section view shows the engagement at the quick-connect receptacle 212B between the femoral provisional implant 214 and elongated connector 115 and shaft 116 of the slap hammer tool. Further, as the handle 104 is slid away from the femoral provisional implant 214, the striking member 124 is struck by the sliding member 126, and provides force in a direction to extract the femoral provisional implant 214 from a mounted location or other position.

Figure 7A:
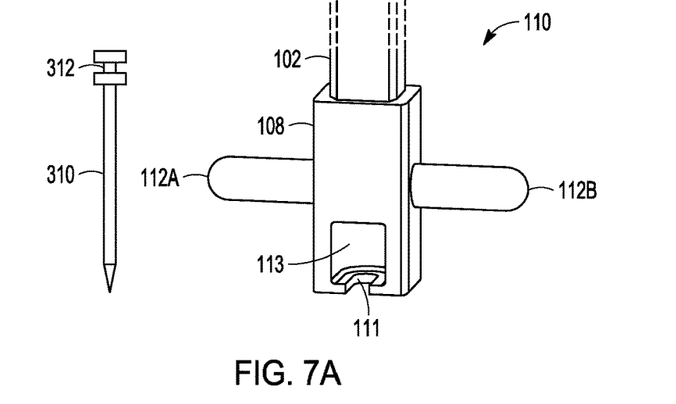
FIG. 7A illustrates a connectable end of a slap hammer instrument configured for coupling with a holding pin according to an example.

The slap hammer tool 100 can also be configured for other uses in addition to uses of the quick coupling mechanism described herein. FIG. 7A provides an illustration of an opposite end of a slap hammer tool, configured for coupling or establishment of a connection with a variety of other instruments. As shown, a second connectable end 110 of a slap hammer tool, such as the slap hammer tool 100 illustrated in FIG. 1, can be configured for coupling or other connection with a second connectable end 110 to instruments such as: a holding pin 310, depicted in FIG. 7A; a femoral inserter/extractor 320, depicted in FIG. 7B; a pin puller 330, depicted in FIG. 7C; and a modular T-handle 340, depicted in FIG. 7D. For example, the second connectable end 110 of the slap hammer tool can provide a channel 111 with an opening 113 configured to receive and temporarily couple with an instrument such as the holding pin 310. The channel 111 can for example be arranged to fit in a channel space 312 of the holding pin 310.

Figure 7B:
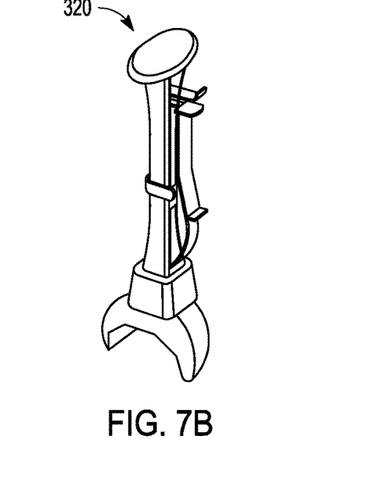
FIG. 7B illustrates a femoral inserter/extractor configured for coupling with a slap hammer instrument according to an example.
Figure 7C:
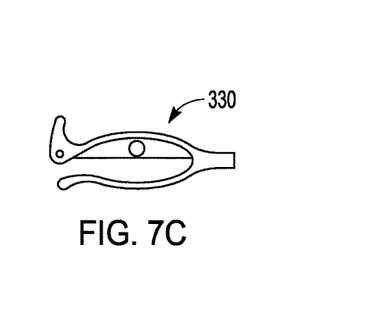
FIG. 7C illustrates a pin puller configured for coupling with a slap hammer instrument according to an example.
Figure 7D:
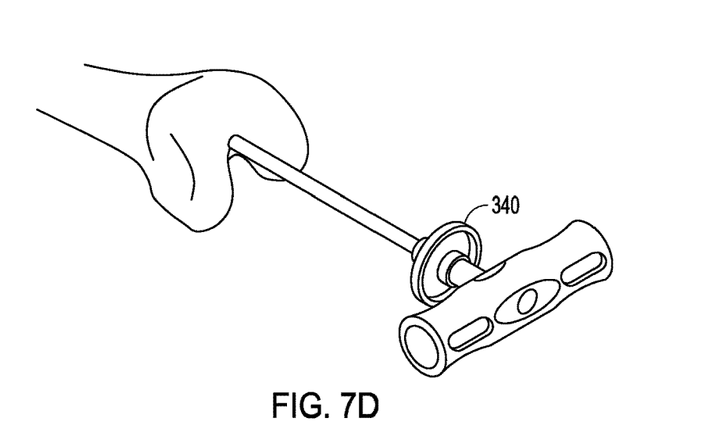
FIG. 7D illustrates a modular t-handle configured for coupling with a slap hammer instrument according to an example.

Alternatively, either or both of the round connector ends 112A, 112B can be used to couple to instruments. For example, one of the round connector ends 112A, 112B of the slap hammer tool can be placed in an extraction hole of the femoral inserter/extractor 320, causing a temporary coupling that enables force to be applied by the slap hammer tool to extract the femoral inserter/extractor 320 from a location. The round connector ends 112A, 112B can likewise be coupled to locations of the pin puller 330 and the modular T-handle 340 to apply directional force as appropriate.

Although the present techniques were described with reference to perform various extraction techniques, by applying a force away from an area of interest, it will be understood that modifications can be made to accept force towards an area of interest in connection with various instrument placement techniques. Moreover, the engageable coupling facilitated by the presently described slap hammer tool and quick connect instrument receptacle can be used to facilitate force and motion in any combination of directions with use of the slap hammer tool.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example.

Thus, the following claims are hereby incorporated into the Detailed Description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A slap hammer, comprising:
a guide shaft having a first end and a second end, the guide shaft coupled to a fixed stop located along the guide shaft between the first end and the second end, the fixed stop including a first stop end and a second stop end;
a connector located rotatably fixed to the first end of the guide shaft; and
a handle positioned around a portion of the guide shaft, the handle configured for slideable movement along the guide shaft between the first end and the second end, the handle including a sliding weight and an opening configured to receive the guide shaft, and wherein the handle is arranged for slideable movement in a first direction to the first stop end of the fixed stop and for slideable movement in a second direction to the second stop end of the fixed stop;
wherein the opening of the handle is configured to correspond to a defined shape of the guide shaft, the defined shape being a non-circular shape, such that rotation of the handle drives a corresponding rotation of the guide shaft and the connector; and
wherein the connector is configured for releasable coupling with an object by insertion of the connector into a receptacle of the object followed by rotation of the handle relative to the object by a fraction of a turn, the fraction of a turn being less than one complete rotation of the handle.

2. The slap hammer of claim 1, further comprising:
a second connector located at the second end of the guide shaft, configured for releasable coupling with a second object.

3. The slap hammer of claim 1, wherein the first stop end of the fixed stop is configured to receive contact from a first striking member positioned within a first side of an interior space of the handle, and wherein the second stop end of the fixed stop is configured to receive contact from a second striking member positioned within a second side of an interior space of the handle.

4. The slap hammer of claim 1, wherein the receptacle is located within a fastener of the object.

5. The slap hammer of claim 4, wherein the fraction of a turn comprises a quarter-turn rotation.

6. The slap hammer of claim 5, wherein the fastener of the object is a quick-connect fastener, and wherein the connector includes an elongated connector configured for releasable coupling with the quick-connect fastener by the rotation of the slap hammer relative to the fastener of the object.

7. A slap hammer, comprising:
a guide rod having a first end and a second end;
a slideable member movable along at least a portion of an area between the first end and the second end of the guide rod, the slideable member rotatably coupled to the guide rod and having an opening configured to correspond to a defined shape of the guide rod, the defined shape being a non-circular shape, such that rotation of the slideable member drives a corresponding rotation of the guide rod;
a striking member configured to provide contact with the slideable member; and
an engagement feature rotatably coupled to the first end of the guide rod such that rotation of the guide rod drives a corresponding rotation of the engagement feature;
wherein the engagement feature is configured for engageable coupling with an instrument, and wherein the engageable coupling is facilitated by insertion of the engagement feature into a receptacle of the instrument followed by rotation of the slideable member and rotatably coupled guide rod relative to the instrument by a fraction of a turn, the fraction of a turn being less than one complete rotation of the slideable member and rotatably coupled guide rod;
wherein the striking member is positioned between the first end and the second end of the guide rod, the slideable member configured to make contact with the striking member within an interior chamber of the slideable member;
wherein upon contact of the slideable member to the striking member when the engageable coupling is established with the instrument, the slap hammer provides a force to the instrument in a direction of movement of the slideable member; and
wherein the engageable coupling can be released by an opposite rotation of the slideable member and rotatably coupled guide rod relative to the instrument.

8. The slap hammer of claim 7, wherein the slideable member is integrated into a handle, wherein the handle is slideably movable along the guide rod in response to user manipulation.

9. The slap hammer of claim 8, wherein the handle includes a weight within the handle, the weight arranged to provide force to the striking member during contact between the slideable member and the striking member.

10. The slap hammer of claim 7, wherein the engagement feature includes a shaft and an elongated connector configured for releasable coupling with a quick connector positioned in the receptacle of the instrument.

11. The slap hammer of claim 10, wherein the elongated connector extends transverse to a longitudinal axis of the guide rod defined between the first and second ends.

12. The slap hammer of claim 7, wherein the fraction of a turn comprises a quarter-turn rotation.

13. The slap hammer of claim 7, wherein the engagement feature is coupled to the guide rod in a fixed position.

14. A slap hammer, comprising:
a guide rod having a first end and a second end;
a slideable member movable along at least a portion of an area between the first end and the second end of the guide rod, wherein the slideable member is integrated into a handle, the handle rotatably coupled to the guide rod and having an opening sized and structured to receive the guide rod to allow slideable movement of the handle along the guide rod in response to user manipulation, wherein the opening of the handle is configured to correspond to a defined shape of the guide rod, the defined shape being a non-circular shape such that rotation of the handle facilitates a corresponding rotation of the guide rod;
a striking member configured to provide contact with the slideable member, wherein the striking member is positioned between and spaced apart from the first end and the second end of the guide rod, and wherein the slideable member is configured to make contact with the striking member within an interior chamber of the handle; and
an engagement feature rotatably coupled to the first end of the guide rod such that rotation of the guide rod drives a corresponding rotation of the engagement feature, the engagement feature including an elongated connector extending transverse to a longitudinal axis of the guide rod defined between the first and second ends;
wherein the engagement feature is configured for engageable coupling with an instrument, and wherein the engageable coupling is facilitated by insertion of the engagement feature into a receptacle of the instrument followed by rotation of the slap hammer relative to the instrument by a fraction of a turn, the fraction of a turn being less than one complete rotation of the slap hammer; and
wherein upon contact of the slideable member to the striking member when the engageable coupling is established with the instrument, the slap hammer provides a force to the instrument in a direction of movement of the slideable member.

15. A slap hammer system, comprising:
a surgical component; and
a slap hammer comprising:
a guide shaft having a first end and a second end, the guide shaft coupled to a fixed stop, the fixed stop located along the guide shaft between the first end and the second end, the fixed stop including a first stop end and a second stop end;
a connector located at the first end of the guide shaft, the connector extending transverse to a longitudinal axis of the guide shaft defined between the first and second ends; and
a handle positioned around a portion of the guide shaft, the handle configured for slideable movement along the guide shaft between the first end and the second end, the handle including a sliding weight and an opening configured to receive the guide shaft, and wherein the handle is arranged for slideable movement in a first direction to the first stop end of the fixed stop and for slideable movement in a second direction to the second stop end of the fixed stop;

wherein the first stop end of the fixed stop is configured to receive contact from a first striking member positioned within a first side of an interior space of the handle, and wherein the second stop end of the fixed stop is configured to receive contact from a second striking member positioned within a second side of an interior space of the handle; and wherein the opening of the handle is configured to correspond to a defined shape of the guide shaft, the defined shape being a non-circular shape to facilitate rotation of the connector from a rotation of the handle; and wherein the connector is releasably coupleable with the surgical component by insertion of the connector into a receptacle of the surgical component followed by rotation of the handle relative to the surgical component by a fraction of a turn, the fraction of a turn being less than one complete rotation of the handle.

* * * * *

UNITED STATES PATENT AND TRADEMARK OFFICE
CERTIFICATE OF CORRECTION

PATENT NO. : 10,052,145 B2
APPLICATION NO. : 13/758605
DATED : August 21, 2018
INVENTOR(S) : Capek et al.

It is certified that error appears in the above-identified patent and that said Letters Patent is hereby corrected as shown below:

In the Claims

In Column 8, Line 46, in Claim 1, after "connector", delete "located"

Signed and Sealed this
Nineteenth Day of March, 2019

Andrei Iancu
*Director of the United States Patent and Trademark Office*